US00PP27537P2

(12) United States Plant Patent
Snijder

(10) Patent No.: US PP27,537 P2
(45) Date of Patent: Jan. 10, 2017

(54) ***PELARGONIUM* PLANT NAMED 'PEPZ0005'**

(50) Latin Name: *Pelargonium peltatum*
Varietal Denomination: PEPZ0005

(71) Applicant: SYNGENTA PARTICIPATIONS AG, Basel (CH)

(72) Inventor: Ronald Snijder, Enkhuizen (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/757,096

(22) Filed: Nov. 17, 2015

(51) Int. Cl.
*A01H 5/02* (2006.01)

(52) U.S. Cl.
USPC ..... Plt./332

(58) Field of Classification Search
USPC ..... Plt./332
CPC ..... A01H 5/0277
See application file for complete search history.

*Primary Examiner* — Kent L Bell
(74) *Attorney, Agent, or Firm* — Dale Skalla

(57) ABSTRACT

A new *Pelargonium* plant named 'PEPZ0005' particularly distinguished by the pink colored inflorescences held above the medium-green foliage, large single florets, trailing habit and drought tolerant with continuous color through the summer.

1 Drawing Sheet

Latin name of the genus and species of the plant claimed: *Pelargonium peltatum*.

Varietal denomination: 'PEPZ0005'.

BACKGROUND OF THE NEW PLANT

The present invention comprises a new *Pelargonium*, botanically known as *Pelargonium peltatum*, and hereinafter referred to by the variety name 'PEPZ0005'.

'PEPZ0005' is a product of a planned breeding program. The new cultivar 'PEPZ0005' has pink colored inflorescences held above the medium-green foliage, large single florets, trailing habit and drought tolerant with continuous color through the summer.

'PEPZ0005' originates from a hybridization in a controlled breeding program made in 2008, in Caldar, Gran Canaria. The female parent was an unpatented, proprietary plant of *Pelargonium peltatum* parentage, identified as 'k02-7156-6' with lighter rose color florets and smaller more open plant habit when compared to 'PEPZ0005'.

The male parent of 'PEPZ0005' was an unpatented, proprietary plant of *Pelargonium peltatum* parentage, identified as 'k03-8277-8' with more blue-rose colored florets and a more open plant habit when compared to 'PEPZ0005'. The resultant seed was sown in December 2008 in a greenhouse in Hillscheid, Germany.

'PEPZ0005' was selected as one flowering plant within the progeny of the stated cross in April 2009 in a greenhouse in Hillscheid, Germany.

The first act of asexual reproduction of 'PEPZ0005' was accomplished when vegetative cuttings were propagated from the initial selection in December 2009 in a greenhouse in Hillscheid, Germany.

BRIEF SUMMARY OF INVENTION

Horticultural examination of plants grown from cuttings of the plant initiated in December 2009 in Hillscheid, Germany, and continuing thereafter, has demonstrated that the combination of characteristics as herein disclosed for 'PEPZ0005' are firmly fixed and are retained through successive generations of asexual reproduction.

'PEPZ0005' has not been observed under all possible environmental conditions. The phenotype may vary significantly with variations in environment such as temperature, light intensity, and day length.

'PEPZ0005' has not been made publicly available more than one year prior to the filing of this application.

The following traits have been repeatedly observed and are determined to be the basic characteristics of the new variety. The combination of these characteristics distinguishes this *Pelargonium* as a new and distinct variety.

BRIEF DESCRIPTION OF THE PHOTOGRAPHS

The accompanying photographic drawing shows typical flower and foliage characteristics of 'PEPZ0005' with colors being as true as possible with an illustration of this type.

Figure 1:
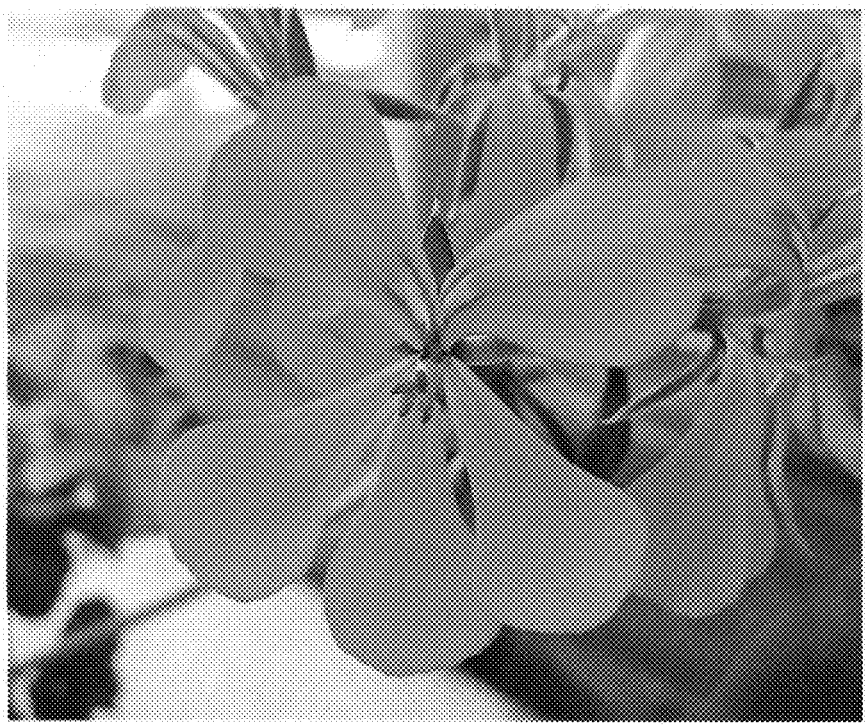
Figure 2:
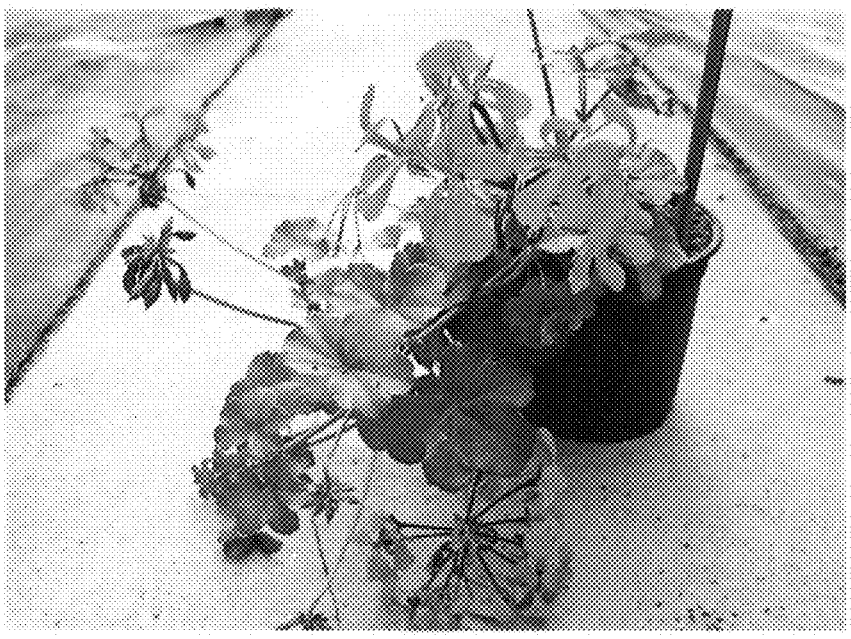

The photographic drawings show in FIG. 1, a close-up of an inflorescence and in FIG. 2, a flowering plant of the new variety.

DETAILED BOTANICAL DESCRIPTION

The plant descriptions and measurements were taken in Enkhuizen, the Netherlands, in early September 2015 under natural light. These plants were approximately 11 weeks old and were grown in 19 cm pots in a greenhouse trial. The plants shown in the photographs were the same plants. Pictures were taken at description moment.

Color references are made to The Royal Horticultural Society Colour Chart (R.H.S.) 2001.

TABLE 1

DIFFERENCES BETWEEN THE NEW VARIETY 'PEPZ0005' AND A MOST SIMILAR VARIETY

| | 'PEPZ0005" | 'Fix 137' (U.S. Plant Pat. No. 21,807) |
|---|---|---|
| Earliness: | Earlier | Later |
| Leaves color: | Medium green | Darker green |
| Flower color: | Pink | White |

Plant:

*Form, growth and habit*.—Trailing, outwardly spreading and drought tolerant with continuous color through the summer, well-branched plant habit.

*Plant height*.—13-20 cm.

*Plant height* (*inflorescence included*).—25-30.0 cm.

*Plant width*.—30-35.0 cm.

Roots:

*Number of days to initiate roots*.—15-18 days at about 22 degrees C.

*Number of days to produce a rooted cutting*.—21-23 days at 22 degrees C.

*Type*.—Fine, fibrous, free branching.

*Color*.—RHS N155B but whiter.

Foliage:

*Immature leaf, color upper surface*.—Closest to RHS 138A.

*Immature leaf, lower surface*.—Closest to RHS 138B.

*Mature leaf, color upper surface*.—Closest to RHS 137B.

*Mature leaf, color lower surface*.—Closest to RHS 137D.

*Length*.—4.3-5.5 cm.

*Width*.—6-7.9 cm.

*Shape*.—Cordate.

*Base shape*.—Cordate.

*Apex shape*.—Acute.

*Margin*.—Slightly dentate.

*Texture upper side*.—Hirsute.

*Texture lower side*.—Sparsely hair, hirsute on veins.

*Leaf zonation color*.—None but kind of circle around leaf base, 1.5 cm diameter, of slightly darker and shinier part.

*Color of veins, upper surface*.—RHS 144A.

*Color of veins, lower surface*.—RHS 137C becoming indistinct.

*Pattern of veining*.—Palmate.

*Petiole color*.—RHS 137C.

*Petiole length*.—2.5-5.5 cm.

*Diameter of petiole*.—0.2 cm.

*Texture*.—Hirsute.

Stem:

*Quantity of branches*.—3.

*Color of stem*.—Between RHS 144A and RHS 144B.

*Length of stem*.—20-30 cm.

*Diameter*.—0.5 cm.

*Length of internodes*.—4.5-6 cm.

*Texture*.—Sparsely hirsute.

Peduncle:

*Color of peduncle*.—RHS 144A.

*Length of peduncle*.—13-18.0 cm.

*Peduncle diameter*.—0.3-0.35 cm.

*Texture*.—Hirsute, glandular hairs.

Pedicel:

*Color of pedicel*.—Upper side: RHS 183B, lower side: RHS 183C with green RHS 144B at base.

*Length of pedicel*.—2.5-3 cm.

*Diameter of pedicel*.—0.15-0.2 cm.

*Texture*.—Sparsely pilose.

Bud (just before opening):

*Color*.—Mix of RHS N57D and RHS 65B, edges and strips of RHS N66A.

*Length*.—2.2 cm.

*Width*.—0.6-0.7 cm.

*Shape*.—Elliptical.

Inflorescence:

*Type*.—Umbel; semi-spherical or nearly semi-spherical.

*Lastingness of individual flowers*.—7-9 days at 18° C. temperature.

*Number of inflorescences per plant*.—12, with immature umbels in various stages.

*Fragrance*.—Spicy.

*Umbel diameter*.—12-14.0 cm.

*Umbel depth*.—6 cm.

Corolla:

*Form*.—Single.

*Number of petals*.—5.

*Diameter of flower*.—About 4 cm length, 2.5 cm wide.

*Depth of flower*.—2-2.5 cm.

*Color upper petals, upper surface*.—RHS N74A but deeper, with RHS 61A veining: 2 stripes with a dot at the top, same color. Space between stripes is filled with RHS 63D.

*Color upper petals, lower surface*.—Closest to RHS 72D but much lighter, stripes of RHS N74A.

*Length of upper petals*.—3.2 cm.

*Width of upper petals*.—1.5 cm.

*Color lower petals, upper surface*.—Closest to RHS N57A but brighter and deeper.

*Color lower petals, lower surface*.—RHS N74A.

*Length of lower petals*.—2.5 cm.

*Width of lower petals*.—1.6 cm.

*Petal shape*.—Obovate to spathulate.

*Apex shape*.—Rounded.

*Margin*.—Entire.

*Base*.—Attenuate.

*Petal texture*.—Papillose on both surfaces.

Calyx:

*Number of sepals*.—5.

*Color of sepals*.—RHS 178A.

*Length of sepals*.—1.5 cm.

*Width of sepals*.—0.3-0.4 cm.

*Sepal shape*.—Lanceolate to linear.

*Apex shape*.—Acute.

*Margins*.—Mostly fused.

*Texture, upper surface*.—Glabrous.

*Texture, lower surface*.—Hirsute.

Reproductive organs:

*Gynoecium*.—Pistil: 1. Length: 1.2 cm. Style color: Closest to RHS 155D. Style length: 0.4 cm. Stigma color: Closest to RHS 71A. Ovary color: Between RHS 144A and RHS 144B. Texture: Velutinous, white hair. Ovary length: 0.4-0.5 cm. Ovary diameter: 0.2 cm.

*Androecium*.—Number of stamens: 7. Color of filaments: RHS N57B with RHS N155C basally. Length filaments: 0.6-1.2 cm. Anther color: Between RHS 83A. Length of anthers: 0.3 cm. Color of pollen: RHS 169B. Pollen amount: Normal.

Fertility/seed set: Has not been determined to date.

Disease/pest resistance: Has not been determined to date.

What is claimed is:

1. A new and distinct variety of *Pelargonium* plant named 'PEPZ0005' substantially as illustrated and described herein.

* * * * *